United States Patent
Corma Canós et al.

(10) Patent No.: US 7,611,623 B2
(45) Date of Patent: *Nov. 3, 2009

(54) SEPARATION METHOD USING AN ITQ-29 ZEOLITE MATERIAL

(75) Inventors: Avelino Corma Canós, Valencia (ES); Fernando Rey Garcia, Valencia (ES); Susana Valencia Valencia, Valencia (ES)

(73) Assignees: Consejo Superior de Investigaciones Cientificas, Madrid (ES); Universidad de Politecnica de Valencia, Valencia (ES)

( * ) Notice: Subject to any disclaimer, the term of this patent is extended or adjusted under 35 U.S.C. 154(b) by 0 days.

This patent is subject to a terminal disclaimer.

(21) Appl. No.: 11/662,762

(22) PCT Filed: Sep. 15, 2005

(86) PCT No.: PCT/ES2005/000500

§ 371 (c)(1), (2), (4) Date: Jul. 11, 2007

(87) PCT Pub. No.: WO2006/035090

PCT Pub. Date: Apr. 6, 2006

(65) Prior Publication Data

US 2007/0261995 A1    Nov. 15, 2007

(30) Foreign Application Priority Data

Sep. 15, 2004  (ES) ............................... 200402255

(51) Int. Cl.
- *C07C 7/13* (2006.01)
- *B01D 53/85* (2006.01)
- *B01D 53/86* (2006.01)

(52) U.S. Cl. .................. 208/310 Z; 423/219; 423/235; 423/239.1; 423/239.2

(58) Field of Classification Search ............. 208/310 Z; 423/219, 235, 239.1, 239.2
See application file for complete search history.

(56) References Cited

U.S. PATENT DOCUMENTS

| 5,292,990 A | 3/1994 | Kantner et al. |
| 5,365,011 A | 11/1994 | Ramachandran et al. |
| 6,200,366 B1 | 3/2001 | Bülow et al. |
| 6,713,041 B1 * | 3/2004 | Moscoso et al. ............ 423/705 |

FOREIGN PATENT DOCUMENTS

EP    1 736 441    12/2006

OTHER PUBLICATIONS

Avelino Corma et al., "Supramolecular self-assembled molecules as organic directing agent for synthesis of zeolites", Nature, vol. 431, pp. 287-290, Sep. 2004.

L. Grace et al., "Recovering Olefins Using Adsorption", Chemical Engineering, vol. 104, n ° 11, pp. 124-125, Nov. 1997.

Ch. Baerlocher et al., "Atlas of Zeolite Framework Types", Fifth Revised Edition, published on behalf of the Structure Commission of the International Zeolite Association, pp. 1-19 and pages having ring structures referred to therein, 2001.

* cited by examiner

*Primary Examiner*—Elizabeth D Wood
(74) *Attorney, Agent, or Firm*—Wenderoth, Lind & Ponack L.L.P.

(57) ABSTRACT

The invention relates to a method of separating the components of a mixture. The inventive method is characterised in that it comprises the following steps: (a) the bringing into contact of the components of a mixture selected from (i) at least two hydrocarbons, (ii) a mixture containing at least nitrogen and oxygen, and (iii) at least one hydrocarbon and water, with an ITQ-29 zeolite material having a T(IV)/T(III) ratio of greater than 7, whereby T(IV) denotes one or more tetravalent elements and T(III) denotes one or more trivalent elements; (b) preferential adsorption of one or more of the components by the ITQ-29 zeolite material and (c) recovery of one or more of the components, preferably for the separation of hydrocarbon mixtures, such as linear or branched olefins from paraffins.

24 Claims, No Drawings

SEPARATION METHOD USING AN ITQ-29 ZEOLITE MATERIAL

TECHNICAL FIELD OF THE INVENTION

The invention pertains to the technical field of microporous crystalline materials of a zeolitic nature, useful as adsorbents in organic compound adsorption and separation processes.

STATE OF THE ART PRIOR TO THE INVENTION

Light olefins are generally obtained by gas oil catalytic cracking, catalytic cracking in the presence of water vapour or by means of what is referred to as the MTO (Methanol to olefins) process. In all of these processes, mixtures of different hydrocarbons are obtained which include linear and branched olefins and paraffins of different molecular weights, said mixture thus having to be put through distilling processes in order to obtain pure hydrocarbons. The particular case of light olefin purification by means of distilling processes is especially difficult due to the relatively low boiling points of these olefins and the similarity thereof with those of the corresponding paraffins. This is especially true in the case of propylene and propane. These problems condition the design of the distilling plants to a mayor degree and inevitably redound in a high-energy consumption in the olefin-production process. Nevertheless, short-chain olefin separation has a major economic impact, given that they are used in different processes in which a high degree of purity is required. Specifically, ethylene and propylene are the raw materials used in the production of plastics and many other chemical compounds. Hence, ethylene is the base reagent for the production of polyethylene, ethylene oxide, chlorovinyl and ethylbenezene, among others. Propylene is used for the production of polypropylene, propylene oxide, acrylonitrile, etc.

The use of molecular sieves, particularly zeolites, is known to be useful in the different hydrocarbon separation processes. Thus, linear paraffins can be separated from branched ones by using zeolites the channels of which are accessible by way of windows formed by 8 tetrahedrons. However, when olefins are present in the hydrocarbon current, these olefins tend to react on the acid centres of zeolites, giving rise to polymerisation products inside the zeolite channels. These products of larger kinetic diameter cannot diffuse toward the exterior of the zeolite, causing the blockage of zeolite pores and therefore reducing the effectiveness thereof in the separation processes.

The acid properties of zeolites stem from the presence of trivalent elements in their composition, which generate a negative charge in the micropore network which is compensated by cations (generally alkaline, alkaline-terrous, organic cations or protons) which are located inside the zeolite channels and cavities. These compensating cations are responsible for the acid properties of these materials, particularly when the cations are protons. In this case, the acid strength of the zeolites may be compared to that of concentrated sulphuric acid. The presence of inorganic cations, such as $Na^+$, $K^+$, $Ca^{2+}$, etc. generates very weak Lewis-type acid centres and are responsible for the elevated hydrophilic properties of these materials, given that the cations tend to coordinate with water molecules. Thus, in addition to the olefin polymerisation problems, these zeolites are seriously limited in their application in separation processes as a result of their elevated hydrophilic properties, given that the water present in the hydrocarbon currents, even in very low concentrations, tends to be absorbed on the cations located inside zeolite channels, thus reducing the effective diameter of its pores. This means that, in separation processes which are carried out with small-pore zeolites (those having channels with openings formed by 8 tetrahedrons), they have to be regenerated rather often or the water eliminated from the hydrocarbon current.

From what is explained above, it is inferred that the use of zeolites with channel openings formed by 8 tetrahedrons with a low content in trivalent elements in their composition would be highly beneficial in olefin separation processes, given that a double objective would be achieved. On one hand, the olefin oligomerisation processes on the inside of the zeolite channels would be avoided, given that acid centres would not be generated. On the other hand, these zeolite materials would not have charge-compensating cations in their channels and would therefore be highly hydrophobic materials. All thereof would redound in a major improvement in the efficiency thereof in processes of separating hydrocarbon currents or gases containing light olefins, even in the presence of major amounts of water.

Zeolites can be classified as extra-large, large, medium or small-pore, depending upon the opening of their channels. Therefore, small-pore zeolites will have channels with openings formed by 8 tetrahedrons, whilst medium-pore zeolites will have 10 tetrahedrons, the large-pored zeolites having 12 and lastly, the extra-large-pore zeolites having channels with openings of more than 12 tetrahedrons.

Zeolite A is a small-pore zeolite which has a three-dimensional channel system with 0.41 nm opening which cross one another forming an almost spherical supercavity measuring 1.14 nm in diameter and a net density of 12.9 tetrahedrons/$nm^3$. This structure has an LTA (Linde Type A) code according to the *Atlas of Zeolite Framework Types* (2001) published by the International Zeolite Association. This porous system imbues this zeolite with a high adsorbing-capacity, but only molecules of small kinetic diameter, such as water, nitrogen, oxygen and linear hydrocarbons, among others, can access the interior thereof.

This zeolite is generally synthesized with Si/Al ratios nearing one, the synthesis thereof up to Si/Al ratios of 3.5, therefore with a high concentration of cations on the inside thereof, having been described. The possibility of synthesizing LTA-structure zeolite with a low aluminium content in its composition and even in absence thereof has made it possible to obtain materials which have no acidity and can therefore be used in separation processes over long periods of time without undergoing olefin polymerisation reactions on their interior.

One of the LTA-structure zeolite materials which are of the properties stated in the immediately preceding paragraph of particular interest, is that known as ITQ-29, which is highly hydrophobic, the efficiency thereof therefore not being reduced in separation processes by adsorption of water, which is generally present in hydrocarbon currents. These two properties have a direct benefit on the separation processes, given that it lengthens the lifetime of the zeolite and lower temperatures and shorter activation times are required in the separation processes of hydrocarbon currents containing light olefins.

ITQ-29 zeolite is described in Spanish patent application P200400662 or in PCT/ES20055/000120.

DESCRIPTION OF THE INVENTION

The invention refers to a method for separating components of a mixture characterized in that it comprises:
(a) bringing into contact of the components of a mixture selected from:
at least two hydrocarbons,
a mixture containing at least nitrogen and oxygen
at least one hydrocarbon and water, with an ITQ-29 zeolite material having a T(IV)/T(III) ratio of greater than 7, whereby T(IV) denotes one or more tetravalent elements and T(III) denotes one or more trivalent elements (b) preferential adsorption of one or more of the components by the ITQ-29 zeolite material and (c) recovery of one or more of the components.

According to the invention, in said separation method, the ITQ-29 zeolite material, which has an LTA structure, has a T(IV)/T(III) ratio of greater than 7, in which T(IV) denotes one or more tetravalent elements, and T(III) denotes one or more trivalent elements. Said ITQ-29 zeolite material of LTA structure preferably has a T(IV)/T(III) ratio of greater than 10. Even more preferably, said ITQ-29 zeolite material of LTA structure has a T(IV)/T(III) ratio of greater than 50.

Additional preferred embodiments of the method are those which are carried out with an ITQ-29 zeolite material of LTA structure which has a T(IV)/T(III) ratio of greater than 200, and even more preferably with the ITQ-29 zeolite material of an LTA structure having a T(IV)/T(III) ratio greater than 2000.

The ITQ-29 material can be prepared essentially as pure silicon dioxide. One particular preferred embodiment of the method refers to a method such as has been defined, in which said ITQ-29 zeolite material in its calcinated form has a composition expressed by a chemical formula in which at least 75% in weight of the total composition is silicon dioxide. Even more preferably, said ITQ-29 zeolite material in its calcinated form has a composition expressed by a chemical formula in which at least 90% in weight of the total composition is silicon dioxide, and in a particularly preferred embodiment, said ITQ-29 zeolite material has a composition expressed by a chemical formula in which at least 98% in weight of the total composition is silicon dioxide.

The mixture which can be separated into its components according to the inventive method can be, for example, a mixture of hydrocarbons containing water.

The mixture of hydrocarbons can contain an olefin as a component which is preferentially adsorbed, and a paraffin as a component which is preferentially not adsorbed.

According to particular embodiments, the mixture is a mixture of hydrocarbons which comprises one or more linear olefins and one or more paraffins.

According to additional particular embodiments, the mixture is a mixture of hydrocarbons which contains an olefin which is propene and a paraffin which is propane.

Other embodiments refer to a mixture comprising an olefin selected from 1-butene, cis-2-butene, trans-2-butene and mixtures thereof and a paraffin which is n-butane.

The mixture can be one which comprises an olefin which is one or more n-pentenes and a paraffin which is n-pentane.

According to additional particular embodiments, the mixture comprises an olefin which is one or more n-hexenes and a paraffin which is n-hexane.

The method can also refer to the separation of a mixture of hydrocarbons which comprises one or more linear hydrocarbons and one or more branched hydrocarbons, for example, a mixture of hydrocarbons which comprises one or more linear olefins and one or more branched olefins. Said linear olefin can be the component which is preferentially adsorbed and the branched olefin the component which is preferentially not adsorbed.

The procedure can also refer to the separation of a mixture of hydrocarbons which comprises one or more branched olefins and one or more branched paraffins.

According to the method, stage c) can comprise the recovery of the component which is preferentially adsorbed, or the recovery of the component which is preferentially not adsorbed.

The component which is preferentially adsorbed can be adsorbed by the ITQ-29 zeolite material of LTA structure in a proportion greater than 70 mg of adsorbate per gram of ITQ-29 zeolite.

According to particular embodiments of the method, the mixture is air which is separated into nitrogen and oxygen. The mixture can also be air which can contain water.

The invention refers to a method such as has been defined, in which the zeolite material is the ITQ-29 zeolite with a low content in trivalent elements in its composition and even without any trivalent elements. This zeolite of these characteristics has very different diffusion factors for linear and branched olefins and for olefins and paraffins, which affords the possibility of its application in methods for separating said hydrocarbons. The efficiency of an adsorbent in separation processes is determined based on the value of the diffusion factors of the products to be separated, termed $R_D$.

Another important parameter in the adsorption properties of the zeolites is their capacity of adsorption in equilibrium, which can be expressed as weight of hydrocarbon adsorbed per unit of weight of adsorbent. The condition of equilibrium is reached when the amount of adsorbate does not increase over time at set hydrocarbon pressure and temperature conditions. In principle, the greater the adsorbing capacity of a zeolite, the smaller the amount which will be required for separating a given amount of hydrocarbon mixture. Thus, in order for a certain separation method to be feasible at a practical level, it is required that the zeolites have high $R_D$ values and high or moderate adsorption capacities.

In this invention, it is shown that the ITQ-29 zeolite with a low content in trivalent elements in its composition and even in absence thereof has different diffusion rates in the adsorption kinetics of different hydrocarbons, such as propane/propene, butanes/butenes, pentanes/pentenes, hexanes/hexenes, with adsorption capacities of greater than 70 $mg_{adsorbate}/g_{zeolite}$ for all of the linear aforementioned hydrocarbons at 1000 mbar and 40° C. Therefore, the ITQ-29 zeolite is a highly suitable adsorbent for carrying out methods for separating paraffins from linear olefins.

Likewise, the ITQ-29 zeolite with low content in trivalent elements in its composition or even in their absence has an adsorption capacity of less than 10 $mg_{adsorbate}/g_{zeolite}$ for branched paraffins or olefins under these same conditions, which also makes the use thereof possible for methods of separating linear from branched olefins. Lastly, the ITQ-29 zeolite used in this invention has a water-adsorption capacity of less than 10 $mg_{water}/g_{zeolite}$, which reveals its hydrophobic nature, enabling the separation of hydrocarbons in presence of major amounts of water.

The separation method of this invention implies that a certain amount of ITQ-29 zeolite material, not having trivalent cations in the composition thereof or in a T(IV)/T(III) ratio greater than 7, is brought into contact with a mixture of gases or liquids, one of which is the desired one or, to the contrary, is the only undesired one, and which is preferentially adsorbed to the interior of the ITQ-29 zeolite. The components of said mixture may be found in gaseous phase or in liquid phase. The mixture of hydrocarbons is kept in contact with the ITQ-29 zeolite material throughout a determined length of time in order to make it possible for the adsorption process to take place and, lastly, the components of the mixture which have not been adsorbed are removed. The component adsorbed in the ITQ-29 zeolite is recovered or eliminated, depending upon whether it is the desired or the only undesired product, by means of techniques such as entraining with another gas or liquid, temperature increase, evacuation or combination of the aforementioned methods.

This separation method an also be carried out in columns, in which case different fronts of products are obtained according to whether they are retained more or less strongly by the ITQ-29 zeolitic bed.

The separation conditions will depend upon the exact composition of the mixture to be separated, but, in principle, must have an upper limit which corresponds, in the case of the separation of mixtures comprised of hydrocarbons, with the start of the thermal cracking reaction of the hydrocarbons, and its freezing point the lower limit. Thus, the process of this invention must preferably be carried out between −100° C. and 300° C., more preferably between −30° C. and 200° C.

Another embodiment comprising the object of invention is the use of an ITQ-29 zeolite which has no trivalent cations in the composition thereof or of a T(IV)/T(III) ratio of greater than 7 for the separation of nitrogen and oxygen from air mixtures. Given that the ITQ-29 zeolite, in particular the aforementioned embodiments, are characterized by their high hydrophobic nature, the separation of nitrogen and oxygen from air mixtures can be carried out in the presence of water.

Below, some examples are provided of the separating properties of different gases employing ITQ-29 zeolite without aluminium in its composition or with a T(IV)/T(III) ratio of greater than 7, where T(IV) refers to tetravalent elements comprised in the structure and T(III) to the trivalent elements which could isomorphically substitute other tetravalent elements in the zeolite net. For this purpose, the adsorption capacity for a variety of linear and branched hydrocarbons has been determined. The examples described below are non-limiting with regard to the scope of the invention.

EXAMPLES

Example 1

Preparation of ITQ-29 Material in Absence of Trivalent Elements

Four grams (4g) of tetra-ethyl-ortho-silicate (TEOS) are added to 16 g of a solution of 4-methyl-2,3,6,7-tetrahydro-IH, 5H-pyride[3,2,1-ij] quinolinium hydroxide (ROH) which contains 0.3 equivalents of hydroxide in 1000 g and 1.75 g of a 25% aqueous tetra-methyl ammonium hydroxide (TMAOH) solution. The mixture is left evaporating in stirring until complete elimination of ethanol from the hydrolysis of TEOS plus the amount of water necessary to reach the final composition indicated. Lastly, 0.38 g of a fluorhydric acid solution (50% HF in weight) is added. The composition of the gel is:

$SiO_2$: 0.25 ROH: 0.25 TMAOH: 0.5 HF: $3H_2O$

The mixture obtained is placed inside an autoclave equipped with a polytetrafluorethylene inner lining and is heated to 135° C. for 7 days. The X-ray diffractogram of the resulting solid indicates that the ITQ-29 material corresponding to the LTA zeolitic structure has been obtained. The calcination at 600° C. in air for 3 hours makes it possible to eliminate the occluded organic species and obtain the purely-siliceous ITQ-29 material capable of being used in adsorption and separation methods.

Example 2

Water Adsorption in ITQ-29 Material Compared to Commercial CaA Zeolite

The measurement of the water-adsorption capacity at 25° C. in the ITQ-29 material, prepared according to Example 1, corresponds to 10 mg/g. On the other hand, the water-adsorption capacity at the same temperature of the commercial CaA zeolite (Molecular Sieves SA, supplied by Aldrich) is 260 mg/g, which proves the high degree of hydrophobicity of the ITQ-29 material.

Example 3

Propene Adsorption in ITQ-29 Material

The measurement of the propene-adsorption capacity of ITQ-29 material, prepared according to Example 1, at 60° C. and 1000 mbar corresponds to 83 mg/g. Likewise, the value found after conducting 20 adsorption/desorption cycles is of 80 mg/g, which proves the ITQ-29 material retains its adsorption capacity, indicating that no oligomerisation processes that block the zeolite pores take place.

Example 4

Propane and Propene Adsorption in ITQ-29 Material

Table 1 provides the propane and propene adsorption capacity values of ITQ-29 material, prepared according to Example 1, at 1000 mbar and different temperatures.

TABLE 1

| T (° C.) | Propane (mg/g) | Propene (mg/g) |
|---|---|---|
| 25 | 95 | 105 |
| 40 | 88 | 92 |
| 50 | — | 88 |
| 60 | 75 | 83 |

The diffusion factor calculated for the adsorption of propene at 60° C. is of $4.32 \times 10^{-4}$ $S^{-1}$, whilst that corresponding to propane at the same temperature is of $9.82 \times 10^{-6}$ $S^{-1}$. Therefore, the factor of the relative adsorption rates of propene as compared denoted by parameter $R_D$, has a value of 44.

Example 5

Butane, 1-butene and isobutene Adsorption in ITQ-29 Material

Table 2 provides the butane, 1-butene and isobutene adsorption capacity values of ITQ-29 material, prepared according to Example 1, at 1000 mbar and different temperatures.

TABLE 2

| T (° C.) | Butane (mg/g) | 1-butene (mg/g) | Isobutene (mg/g) |
|---|---|---|---|
| 25 | — | 135 | — |
| 60 | — | 115 | 7 |
| 80 | 86 | 105 | — |

Worthy of special mention based on the results of the table above is the low isobutene adsorption capacity compared to 1-butene, which proves the potential of the ITQ-29 material for separating linear from branched olefins.

Example 6

Hexane, 1-hexene and 3-methyl pentene Adsorption in ITQ-29 Material

Table 3 provides the hexane, 1-hexene and 3-methyl pentene adsorption capacity values of ITQ-29 material, prepared according to Example 1, at different temperatures.

TABLE 3

| T (° C.) | hexane (mg/g) | 1-hexene (mg/g) | 3-methyl pentene (mg/g) |
|---|---|---|---|
| 25 | 90 | 154 | 1 |
| 80 | 88 | — | — |

Worthy of special mention based on the results of the Table is the low 3-methyl pentene adsorption capacity compared to the 1-hexene, which once again shows the potential of ITQ-29 material for separating linear from branched olefins.

The invention claimed is:

1. A method for separating components of a mixture wherein said method comprises:
   (a) bringing into contact the components of a mixture selected from:
      at least two hydrocarbons,
      a mixture containing at least nitrogen and oxygen, and
      at least one hydrocarbon and water, with an ITQ-29 zeolite material having a T(IV)/T(III) ratio of greater than 7, whereby T(IV) denotes one or more tetravalent elements and T(III) denotes one or more trivalent elements
   (b) preferential adsorption of one or more of the components by ITQ-29 zeolite material and
   (c) recovery of one or more of the components.

2. A separation method according to claim 1, wherein said ITQ-29 zeolite material has a T(IV)/T(III) ratio of greater than 10, in which T(IV) denotes one or more tetravalent elements and T(III) denotes one or more trivalent elements.

3. A separation method according to claim 1, wherein said ITQ-29 zeolite material has a T(IV)/T(III) ratio of greater than 50.

4. A separation method according to claim 1, wherein said ITQ-29 zeolite material of LTA structure has a T(IV)/T(III) ratio of greater than 200.

5. A separation method according to claim 1, wherein said ITQ-29 zeolite material has a T(IV)/T(III) ratio of greater than 2000.

6. A method according to claim 1, wherein said ITQ-29 zeolite material in its calcinated form has a composition expressed by a chemical formula in which at least 75% in weight of the total composition is silicon dioxide.

7. A method according to claim 1, wherein said ITQ-29 zeolite material in its calcinated form has a composition expressed by a chemical formula in which at least 90% in weight of the total composition is silicon dioxide.

8. A method according to claim 1, wherein said ITQ-29 zeolite material in its calcinated form has a composition expressed by a chemical formula in which at least 98% in weight of the total composition is silicon dioxide.

9. A method according to claim 1, wherein the mixture is a mixture of hydrocarbons containing water.

10. A method according to claim 1, wherein the mixture of hydrocarbons contains an olefin as a component which is preferentially adsorbed and a paraffin as a component which is preferentially not adsorbed.

11. A method according to claim 1, wherein the mixture is a mixture of hydrocarbons which comprises one or more linear olefins and one or more paraffins.

12. A method according to claim 1, wherein the mixture is a mixture of hydrocarbons which comprises an olefin which is propene and a paraffin which is propane.

13. A method according to claim 1, wherein the mixture is a mixture comprises an olefin selected from 1-butene, cis-2-butene, trans-2-butene and mixtures thereof, and a paraffin which is n-butane.

14. A method according to claim 1, wherein the mixture comprises an olefin which is one or more n-pentenes and a paraffin which is n-pentane.

15. A method according to claim 1, wherein the mixture comprises an olefin which is one or more n-hexenes and a paraffin which is n-hexane.

16. A method according to claim 1, wherein the mixture is a mixture of hydrocarbons which comprises one or more linear hydrocarbons and one or more branched hydrocarbons.

17. A method according to claim 1, wherein the mixture is a mixture of hydrocarbons which comprises one or more linear olefins and one or more branched olefins.

18. A method according to claim 1, wherein the mixture of hydrocarbons which comprises one or more linear paraffins and one or more branched paraffins.

19. A method according to claim 1, wherein the mixture of hydrocarbons contains a linear olefin as the component which is preferentially adsorbed and a branched olefin as the component which is preferentially not adsorbed.

20. A method according to claim 1, wherein stage (c) comprises the recovery of the component which is preferentially adsorbed.

21. A method according to claim 1, wherein stage (c) comprises the recovery of the component which is preferentially not adsorbed.

22. A method according to claim 1, wherein stage (c) comprises the recovery of the component which is preferentially adsorbed, said component being adsorbed by the ITQ-29 zeolite material in a proportion greater than 70 $mg_{adsorbate}/g_{zeolite}$.

23. A method according to claim 1, wherein the mixture is air.

24. A method according to claim 1, wherein the mixture is air containing water.

* * * * *